United States Patent [19]

Epstein et al.

[11] Patent Number: 5,556,434
[45] Date of Patent: Sep. 17, 1996

[54] REPLACEMENT HIP JOINT

[76] Inventors: Norman Epstein, Rte. No. 301, Carmel, N.Y. 10512; Steven B. Zelicof, 12 Seneca Rd., Scarsdale, N.Y. 10583

[21] Appl. No.: 398,891

[22] Filed: Mar. 6, 1995

[51] Int. Cl.[6] ........................................... A61F 2/34
[52] U.S. Cl. ........................................... 623/22; 623/18
[58] Field of Search ........................ 623/18, 19, 20, 623/21, 22, 23

[56]  References Cited

U.S. PATENT DOCUMENTS

| 4,179,758 | 12/1979 | Gristina | 623/19 |
|---|---|---|---|
| 4,770,661 | 9/1988 | Oh | 623/23 |
| 5,171,285 | 12/1992 | Broderick | 623/22 |
| 5,192,329 | 3/1993 | Christie et al. | 623/22 |
| 5,201,769 | 4/1993 | Schutzer | 623/23 |
| 5,902,898 | 3/1992 | Bekki et al. | 623/22 |

Primary Examiner—David Isabella
Attorney, Agent, or Firm—Parmelee, Bollinger & Bramblett

[57]  ABSTRACT

Three axis movement emulating the action of a natural hip joint is provided by a universal assembly mounted on movable roller bearings in a horizontal swivel. A stem attached to the universal assembly is adapted to be implanted in the femur of the user. The horizontal swivel is mounted on roller bearings in a spherical housing which is adapted to be inserted in the acetabulum of the user.

13 Claims, 2 Drawing Sheets

REPLACEMENT HIP JOINT

FIELD OF THE INVENTION

This invention relates to artificial ball and socket joints, and more particularly to such joints which provide a replacement joint for a human hip.

BACKGROUND OF THE INVENTION

The human hip joint may be fractured, severely damaged or deteriorated by progressive disease such as osteoarthritis, thereby requiring repair or total hip replacement. In the latter the natural femoral head and neck are removed and an acetabular cup is secured to the acetabulum of the patient. A metal ball is received in the cup to provide the desired universal motion and the ball is coupled to a stem implanted in the femur of the user. Although constructions in the replacement hip joints vary, in most such joints a metal surface bears and moves on a plastic surface which is subject to wear and tear. This results in the deposition of debris in the hip area and eventually a total breakdown of the joint. In addition, limitations are also placed on the movement in the replaced joint, possibly resulting in hip dislocation or premature wear.

SUMMARY OF THE INVENTION

Accordingly, it is an object of this invention to provide a new and improved replacement hip joint which simulates the three axes movement of the natural hip joint and may be installed using presently used surgical procedures.

Another object of this invention is to provide a new and improved replacement hip joint which reduces friction in providing joint movement, thereby reducing wear and tear and increasing the longevity of the replacement joint.

In carrying out this invention in one illustrative embodiment thereof, an artificial hip joint housing which is adapted to be positioned in the acetabulum of the user has a horizontal swivel housed therein. A first movable bearing means mounts the horizontal swivel for movement in said hip joint housing. A universal assembly is moveably mounted in the horizontal swivel by a second movable bearing means. A stem which is adapted to be implanted in the femur of the user is mounted on said universal assembly whereby movement of the stem created by movement of the leg of the user is applied to the universal assembly in said horizontal swivel, which combined will simulate the movement of a natural hip.

BRIEF DESCRIPTION OF THE DRAWINGS

This invention together with further objects, aspects, features and advantages thereof will be more fully understood from the following description taken in connection with the accompanying drawings.

DESCRIPTION OF THE PREFERRED EMBODIMENTS

Figure 1:
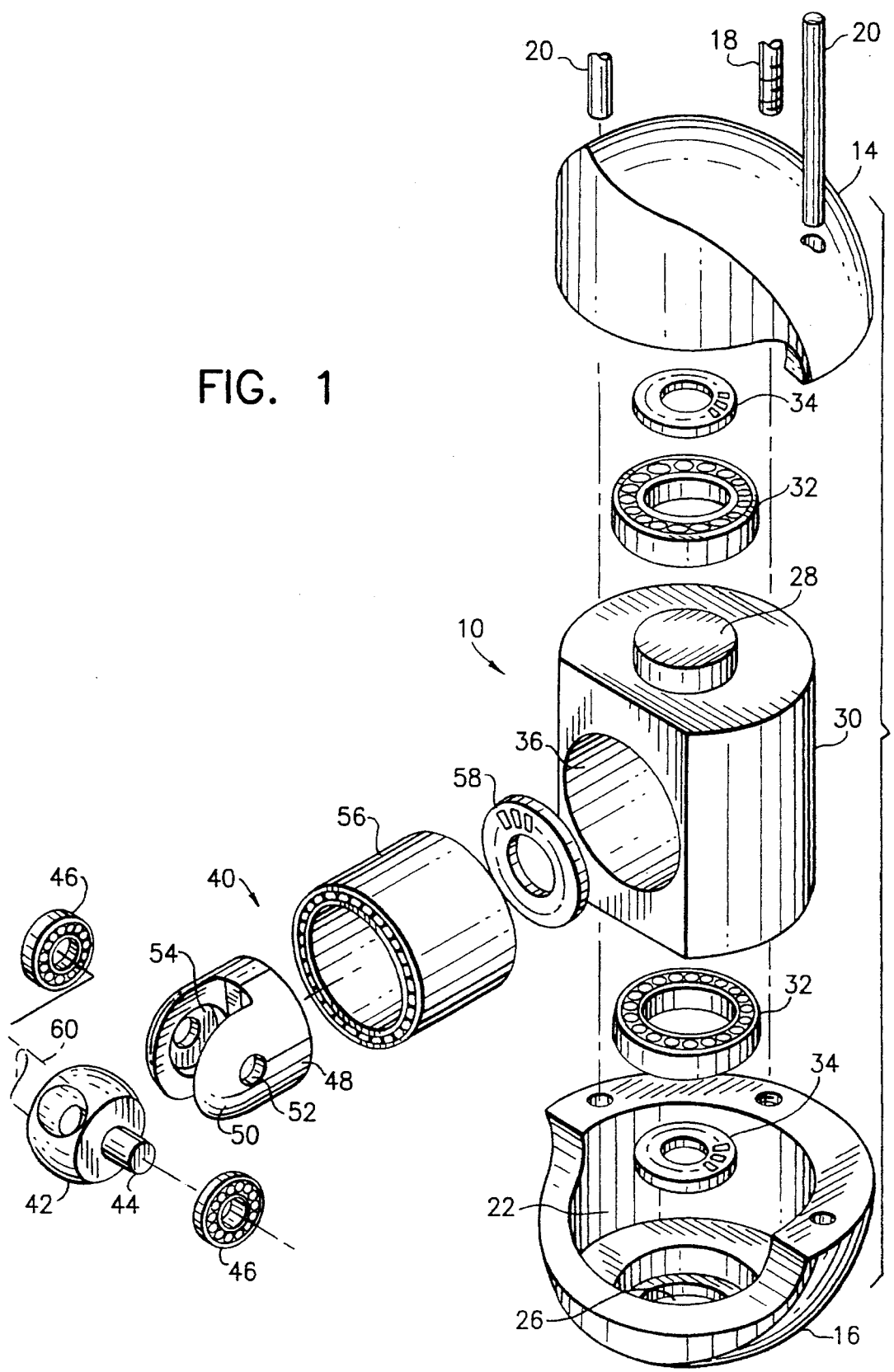
FIG. 1 is an exploded perspective view of the replacement hip joint of the present invention.
Figure 2:
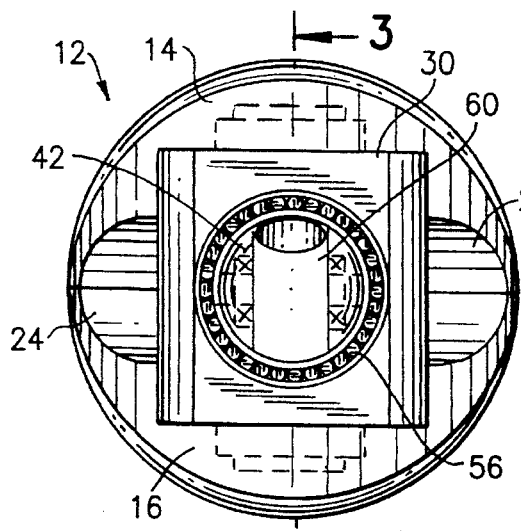
FIG. 2 is a front elevational view of the assembled replacement hip joint of FIG. 1.

Referring now to FIG. 1 an artificial hip joint, referred to generally with the reference numeral 10, has a hollow split housing 12 with a top half housing 14 and bottom half housing 16. The top and bottom half housings 14 and 16 are assembled by a screw 18 and alignment pins 20 to form a generally spherical hip joint housing 12 having a generally cylindrical opening 22 therein flanked by spherical extension openings 24 to accommodate assembly and movement of the artificial hip joint 10 in the housing 12.

Figure 3:
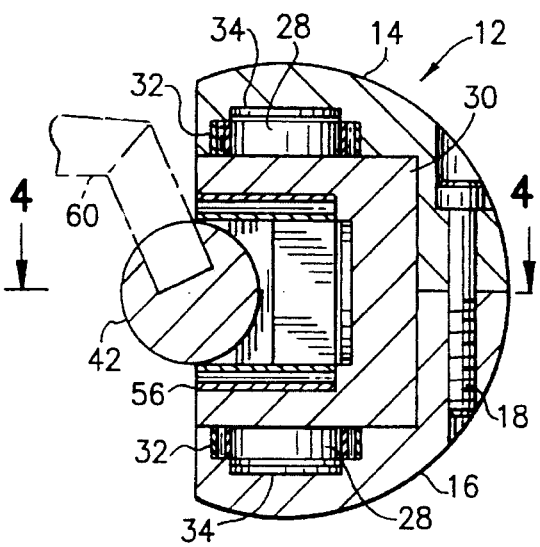
FIG. 3 is a cross-sectional view taken along line 3—3 in FIG. 2.
Figure 5:
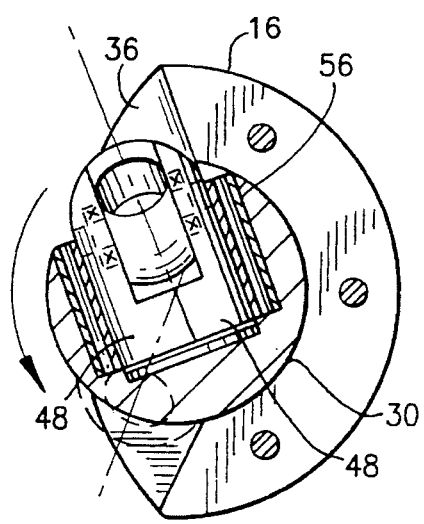
FIG. 5 is similar to FIG. 4, illustrating the rotation of the universal assembly in the horizontal swivel in the hip joint housing of the present invention.

The top and bottom split half housings 14 and 16 each have a well 26 as is best seen in the bottom half housing 16 of FIG. 1. A horizontal swivel 30 has mounting studs 28 on the top and bottom thereof (see FIG. 3). The mounting studs 28 carry roller bearings 32 and are mounted in housing wells 26 on thrust bearings 34 (see FIGS. 1 and 3). Accordingly, the horizontal swivel is mounted for substantially friction free rotational movement in said hip joint housing 12 (See FIG. 5).

Figure 4:
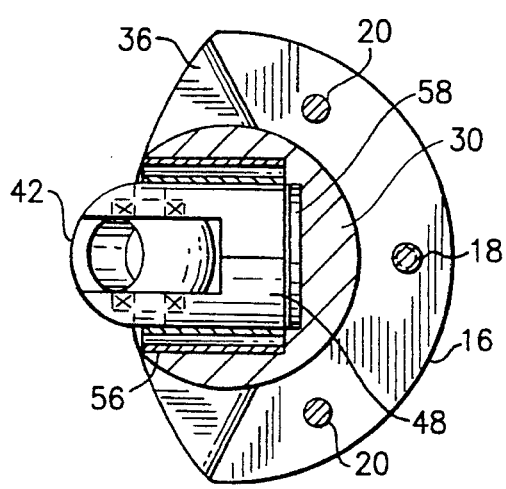
FIG. 4 is a cross-sectional view taken along line 4—4 of FIG. 3.

The generally cylindrical horizontal swivel 30 has a central opening 36 which houses a universal assembly, referred to generally with the reference numeral 40. The universal assembly 40 includes a truncated spherical ball 42 on an axle 42, roller bearings 46, a split head 48 having ears 50 with openings 52 therethrough and sockets 54 therein, roller bearings 56 and thrust bearings 58. An elongated stem 60 is mounted in the truncated spherical ball 40. The stem 60 is adapted to be implanted in the femur of the user so that the motion of the femur is translated by the universal assembly 40 and the horizontal swivel 30 to simulate the movement which would have taken place in a natural hip joint in an almost friction free manner. The axle 44 carrying the ball 42 and the stem 60 is mounted in the ear openings 52 on roller bearings 46 positioned in sockets 54 of the ears 50 of the split head 48. The split head 48 is positioned on roller bearings 56 and thrust bearings 58 in the horizontal swivel 30. The universal assembly 40 is assembled in the horizontal swivel 30 through opening 36 therein (See FIG. 4).

In the preferred form of this invention, the above described artificial hip joint 10 is used as a replacement for the natural joint, necessitating the removal of the femoral head and neck. The elongated stem 60 is implanted or inserted in the femur of the user and the spherical housing 12 is inserted in the prepared acetabulum. This installation will permit a sliding movement in the acetabulum promoting lubrication thereof by synovial fluids, thereby inhibiting further deterioration of the joint. The normal compressive force of the weight of the patient along with the soft tissue tension around the hip will retain the joint in the acetabulum. In the event that the acetabulum is so diseased that the direct mounting of the housing of the joint in the acetabulum is not feasible, the housing may be cemented or press fit into the acetabulum. The size of the artificial joint will vary in accordance with the size of the socket of the user in which the joint is inserted. The component joint is preassembled and removably attached to the stem for ease of use in the operating room.

Accordingly, a very compact, substantially friction free artificial joint is provided which simulates the actual movement in a natural joint. In addition, the artificial hip joint of the present invention requires no additional medical measures and may be used in accordance with standard hip replacement procedures.

Since other modifications and changes varied to fit particular operating requirements and environments will be apparent to those skilled in the art, the invention is not considered limited to the examples chosen for purposes of disclosure and covers all modifications and changes which do not constitute departures from the true spirit and scope of this invention.

What is claimed is:

1. An implantable artificial hip joint adapted to be inserted in a cavity of a natural acetabulum to simulate three axis of movement of a natural hip, said hip joint comprising:

an artificial hip joint housing configured to be positioned in the acetabulum of the user;

a horizontal swivel means having a central opening therein rotatably disposed within said hip joint housing;

a first rotatable bearing means for movably mounting said horizontal swivel means in said joint housing;

a universal assembly housed in said central opening of said horizontal swivel;

a second rotatable bearing means for movably mounting said universal assembly in said central opening of said horizontal swivel means; and a stem removably mounted to said universal assembly, said stem configured to be implanted in the femur of the user whereby movement of said stem is translated into movement by said universal assembly and said horizontal swivel to simulate movement of the natural hip.

2. The artificial hip joint as claimed in claim 1 wherein said hip joint housing is a split housing having a top half and a bottom half which are joined by at least one screw.

3. The artificial hip joint as claimed in claim 1 wherein said horizontal swivel is generally cylindrical and terminating at opposite ends having a mounting stud on each end thereof.

4. The artificial hip joint as claimed in claim 2 wherein said top and bottom halves of said split housing each having a recess formed therein and said horizontal swivel having opposite ends and mounting studs on said opposite ends thereof which are positioned in said recesses.

5. The artificial hip joint as claimed in claim 4 wherein said first rotatable bearing means include roller and thrust bearing means positioned in said recesses in said housing for supporting said studs of said horizontal swivel for substantially friction free movement of said horizontal swivel in said recesses of said split housing.

6. The artificial hip joint as claimed in claim 1 wherein said second rotatable bearing means comprises roller and thrust bearing means.

7. The artificial hip joint as claimed in claim 1 wherein said universal assembly includes:

a truncated ball mounted on an axle;

an elongated stem mounted in said ball adapted to be attached to the femur of the user; and a split head having ears extending therefrom carrying said axle for rotation in said ears.

8. The artificial hip joint as claimed in claim 6 wherein said second movable bearing means comprises thrust bearings means in said opening of said horizontal swivel into which said split head is assembled and roller bearing means surrounding said split head in said opening of said horizontal swivel.

9. The artificial hip joint as claimed in claim 7 wherein said ears of said split head have sockets therein for receiving roller bearing means surrounding said axle mounted therein.

10. An implantable artificial hip joint adapted to be inserted in a cavity of a natural acetabulum to simulate three axis of movement of a natural hip, said hip joint comprising:

an artificial hip joint split housing having a top half and a bottom half configured to be positioned in the acetabulum of the user;

a generally cylindrical horizontal swivel means having an opening and terminating at opposite ends and having a mounting stud on each end thereof housed in said hip joint housing;

a recess formed in each of said top and bottom halves of said split housing;

a first rotatable bearing means positioned in said recesses for movably mounting said horizontal swivel means in said joint housing with said mounting studs positioned on said first rotatable bearing means in said recesses;

a universal assembly housed in said opening of said horizontal swivel means;

a second rotatable bearing means for movably mounting said universal assembly in said opening of said horizontal swivel means; and a stem removably mounted on said universal assembly, said stem configured to be implanted in the femur of the user whereby movement of said stem is translated into movement by said universal assembly and said horizontal swivel to simulate movement of the natural hip.

11. The artificial hip joint as claimed in claim 10 wherein said universal assembly includes:

a truncated ball mounted on an axle;

an elongated stem mounted in said ball adapted to be attached to the femur of the user; and a split head having ears extending therefrom carrying said axle for rotation in said ears.

12. The artificial hip joint as claimed in claim 11 wherein said second rotatable bearing means comprises thrust bearings means in said opening of said horizontal swivel into which said split head is assembled and roller bearing means surrounding said split head in said opening of said horizontal swivel.

13. The artificial hip joint as claimed in claim 11 wherein said ears of said split head have sockets therein for receiving roller bearing means surrounding said axle mounted therein.

* * * * *